US012667536B2

(12) United States Patent
Fukuhara et al.

(10) Patent No.: US 12,667,536 B2
(45) Date of Patent: Jun. 30, 2026

(54) HAIR TREATMENT METHOD

(71) Applicant: KAO CORPORATION, Tokyo (JP)

(72) Inventors: Masaki Fukuhara, Arakawa-ku (JP); Hiroko Okabe, Kokubunji (JP)

(73) Assignee: KAO CORPORATION, Tokyo (JP)

( * ) Notice: Subject to any disclaimer, the term of this patent is extended or adjusted under 35 U.S.C. 154(b) by 895 days.

(21) Appl. No.: 17/621,857

(22) PCT Filed: Jun. 25, 2020

(86) PCT No.: PCT/JP2020/024987
§ 371 (c)(1),
(2) Date: Dec. 22, 2021

(87) PCT Pub. No.: WO2020/262525
PCT Pub. Date: Dec. 30, 2020

(65) Prior Publication Data

US 2022/0233428 A1 Jul. 28, 2022

(30) Foreign Application Priority Data

Jun. 26, 2019 (JP) ................................ 2019-118586

(51) Int. Cl.

| | |
|---|---|
| ***A61K 8/898*** | (2006.01) |
| ***A61K 8/20*** | (2006.01) |
| ***A61K 8/34*** | (2006.01) |
| ***A61K 8/41*** | (2006.01) |
| ***A61Q 5/10*** | (2006.01) |

(52) U.S. Cl.
CPC ................ *A61K 8/898* (2013.01); *A61K 8/20* (2013.01); *A61K 8/34* (2013.01); *A61K 8/345* (2013.01); *A61K 8/41* (2013.01); *A61Q 5/10* (2013.01); *A61K 2800/432* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 2006/0140900 | A1 | 6/2006 | Watanabe et al. |
| 2010/0310491 | A1 | 12/2010 | Falk et al. |
| 2013/0164390 | A1 | 6/2013 | Richards et al. |

FOREIGN PATENT DOCUMENTS

| | | | |
|---|---|---|---|
| CN | 1679475 | A | 10/2005 |
| CN | 1742701 | A | 3/2006 |
| CN | 102548527 | A | 7/2012 |
| CN | 105816341 | A | 8/2016 |
| JP | 2001-220322 | A | 8/2001 |
| JP | 2002-241236 | A | 8/2002 |
| JP | 2004-35434 | A | 2/2004 |
| JP | 2006-206585 | A | 8/2006 |
| JP | 2011-503059 | A | 1/2011 |
| JP | 2015-502406 | A | 1/2015 |
| JP | 2016-104706 | A | 6/2016 |
| JP | 2020-66575 | A | 4/2020 |
| WO | WO 2018/031941 | A1 | 2/2018 |
| WO | WO 2020/022488 | A1 | 1/2020 |

OTHER PUBLICATIONS

Martin, How to Soften Hair After Dyeing, https://web.archive.org/web/20171223205807/https://www.wikihow.com/Soften-Hair-After-Dyeing#/Image:Care-for-Fine-Hair-Step-4-Version-3.jpg (Year: 2017).*
Momentive, Silsoft CLX-E Conditioning Agent Marketing Bulletin, Apr. 2017 (Year: 2017).*
JP2004035434 Google Translation of Table 1 (Year: 2004).*
International Search Report mailed on Aug. 25, 2020 in PCT/JP2020/024987 filed on Jun. 25, 2020 (3 pages).
ID 6252145, "Conditioner", Mintel GNPD [online], Jan. 2019, [retrieved on Aug. 12, 2020], retrieved from the Internet: <URL: https://portal.mintel.com>, pp. 1-3 (with partial English Translation).
ID 6281789, "Smooth Effect Chemistry Free Conditioner", Mintel GNPD [online], Jan. 2019, [retrieved on Aug. 12, 2020], retrieved from the Internet: <URL: https://portal.mintel.com>, pp. 1-3 (with partial English Translation).
ID 6414845, "Smooth Effect Chemistry Free Hair Mask", Mintel GNPD [online], Mar. 2019, [retrieved on Aug. 12, 2020], retrieved from the Internet: <URL: https://portal.mintel.com>, pp. 1-4 (with partial English Translation).
ID 6252141, "Hair Mask", Mintel GNPD [online], Jan. 2019, [retrieved on Aug. 12, 2020], retrieved from the Internet: <URL: https://portal.mintel.com>, pp. 1-4 (with partial English Translation).
Extended European Search Report dated Jun. 9, 2023 in European Application 20832077.0, 9 pages.
Database GNPD [Online]Mintel; May 29, 2019, anonymous: "Protection Serum CC Cream", Database Accession No. 6575323, XP 93048358A, 4 pages.

* cited by examiner

*Primary Examiner* — Jennifer A Berrios
(74) *Attorney, Agent, or Firm* — Oblon, McClelland, Maier & Neustadt, L.L.P.

(57) ABSTRACT

A method for treating hair, comprising steps 1 and 2 below:
(step 1) applying a hair dye composition to hair to dye the hair; and
(step 2) applying a hair treatment agent to the hair subjected to hair dyeing in the step 1, the hair treatment agent comprising the following components (A), (B) and (C) and having a pH of 4 or less or 8 or more:
(A) an epoxy-aminosilane copolymer which is a reaction product of the following compounds (a) to (d):
(a) a polysiloxane having at least two oxiranyl groups or oxetanyl groups;
(b) a polyether having at least two oxiranyl groups or oxetanyl groups;
(c) an aminopropyltrialkoxysilane; and
(d) a specific primary and secondary amines;
(B) water; and
(C) a pH adjuster.

11 Claims, No Drawings

HAIR TREATMENT METHOD

FIELD OF THE INVENTION

The present invention relates to a hair treatment method performed after hair dyeing.

BACKGROUND OF THE INVENTION

In recent years, in addition to chemical treatment such as hair color and permanent, damages in the hair tip portion have become more serious, particularly due to hair styling using heat such as a hair iron or a hair dryer, which has become popular among young women. In hair with accumulated damage by these complex hair care habits, deterioration of the appearance characteristics found in healthy hair such as luster, hair manageability, and color depth has been caused, which has become more problematic for consumers. Further, when hair dyeing is performed on the hair with accumulated such hair damages, the dyed hair color can easily turn dull and the original vivid color accompanying the dyed hair is impaired.

For this reason, several techniques have been proposed for repairing the appearance deterioration of hair in which damage has accumulated. For example, Patent Literature 1 discloses a hair cosmetic containing a specific cationic polymer and a specific anionic polymer, facilitating improvement of the feeling and appearance of damaged hair like toward healthy hair. Patent Literature 2 discloses a method for elevating chroma of hair by washing the hair with an aqueous shampoo containing a water-insoluble silicone having an amino group or a quaternary ammonium group in the molecule under a solubilized state, and then treating the hair with an aqueous conditioner containing a higher alcohol and a cationic surfactant in a constant ratio. Patent Literature 3 discloses a hair care composition containing a composition containing a combination of specific plant serum fractions, which elevates richness and density of the hair appearance and reduces the appearance of white hair. Patent Literature 4 discloses a hair cosmetic containing an organic carboxylic acid, phenoxyethanol and a specific organic solvent, which imparts luster and vividness to damaged hair. Patent Literature 5 discloses a hair transparency improver which contains an agent which increases the weight of damaged hair by 2 to 30 wt % as an active ingredient.

Patent Literature 6 discloses a method for imparting a conditioning effect by a personal care composition containing a reaction product of a specific oxirane or oxetane compound and a specific aminosilane compound (i.e., epoxy aminosilane copolymer) to restore hydrophobicity of damaged hair.

(Patent Literature 1) JP-A-2016-104706
(Patent Literature 2) JP-A-2006-206585
(Patent Literature 3) JP-A-2015-502406
(Patent Literature 4) JP-A-2004-35434
(Patent Literature 5) JP-A-2001-220322
(Patent Literature 6) JP-A-2011-503059

SUMMARY OF THE INVENTION

The present invention provides a method for treating hair, comprising the following steps 1 and 2:

(Step 1) applying a hair dye composition to the hair to dye the hair; and (Step 2) applying a hair treatment agent to the hair subjected to hair dyeing in the step 1, the hair treatment agent having a pH of 4 or less or 8 or more and comprising the following components (A), (B) and (C):

(A) an epoxy-aminosilane copolymer, which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3 amino-9-ethylcarbazole, 1-aminoheptafluorohexane, 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide, polymer amines (B) water; and (C) a pH adjuster.

The present invention further provides a kit for hair treatment, comprising a hair dye composition and the above hair treatment agent.

The present invention further provides a post-hair-dyeing treatment agent, comprising the components (A), (B) and (C) and having a pH of 4 or less or 8 or more.

The present invention further provides a method for enhancing chroma of a color of dyed hair, comprising implementing the above step 2 on hair after dyeing.

DETAILED DESCRIPTION OF THE INVENTION

The technique described in Patent Literature 1 can provide an effect of improving the feel and the gloss of hair, but may not enhance the vividness of the color of hair. The technique described in Patent Literature 2 can enhance the chroma of hair to improve vividness, but may not be sufficient for improving of vividness in single use or the resistance against washing with shampoo or the like. The technique described in Patent Literature 3 is a technique for improving the appearance of hair by physiologically acting on the scalp to change the conditions of newly growing hair, and has a problem that it takes a long time to exhibit an effect. The techniques described in Patent Literatures 4 and 5 exhibit an effect on heavily damaged hair such as cavities caused in the hair, and may not provide an effect for hair with no cavities. The technique described in Patent Literature 6 serves to form a robust hydrophobic film on hair to impart an excellent conditioning effect to hair with accumulated damage, but it does not disclose whether it enhances the vividness of the color of dyed hair by applying to hair after hair dyeing.

Accordingly, the present invention relates to a method for treating hair, which can readily and quickly enhance the vividness of the color of dyed hair when applied to dyed hair, and a hair treatment agent for use in the method.

The present inventors found that treatment of dyed hair with a hair cosmetic composition containing a reaction product of a specific oxirane or oxetane compound and a specific aminosilane compound (i.e. epoxy-aminosilane copolymer) and having a specific acidic pH or basic pH serves to enhancement of the vividness of the color of dyed hair and duration of the effect thereof without being impaired even after repeated hair washing. In this way, the present invention was completed.

The method for treating hair according to the present invention serves to enhancement of the vividness of the color of dyed hair, and duration of the effect thereof even after repeated hair washing.

Step 1

The step 1 is a step of applying a hair dye composition to hair to dye the hair.

The hair dye composition is not particularly limited, and all types of hair dye compositions can be used such as semipermanent hair dye materials containing a dye directly, such as color treatments and hair manicures; permanent hair dyes such as oxidation hair dyes containing a first agent containing an alkali agent and an oxidation dye precursor and a second agent containing an oxidizing agent and non-oxidation hair dyes which create a color by reaction of iron ions with phenol; and temporary hair dye materials containing a pigment and a film agent, such as hair mascaras, hair foundations and hair color sprays. The form thereof may be any of a cream, a liquid, a foam and the like.

From the viewpoint of more readily enhancing the vividness of the color of dyed hair, it is preferable that rather than a temporary hair dye material which covers the hair with a film agent or the like, a semipermanent hair dye material or a permanent hair dye capable of dyeing the inside of hair, more preferably a permanent hair dye, be applied to the hair to dye the hair in the step 1.

The method for dyeing hair is not limited, and a hair dye composition may be applied to the hair in accordance with a usual method. If necessary, the dyed hair may be left to stand for a predetermined time, followed by rinsing the dyed hair, and appropriately performing washing with shampoo, rinsing and the like. Thereafter, the hair may be appropriately dried with a towel to remove excess water, followed by proceeding to the step 2 without drying, or the hair may be dried with a dryer or naturally, followed by proceeding to the step 2. From the viewpoint of improving the compatibility of a hair treatment agent with hair to obtain good uniform application properties in the step 2, it is preferable to implement the step 2 on hair brought into a state of wet hair.

In the present invention, the wet hair refers to hair moderately soaked with water, and corresponds to, for example, hair rinsed with flowing water, and then appropriately dried with a towel to remove excess water. From the viewpoint of improving the compatibility of a hair treatment agent with hair to obtain good uniform application properties in the step 2, the water content of wet hair is preferably 0.2 g or more, more preferably 0.25 g or more, further more preferably 0.3 g or more, and preferably 1 g or less, more preferably 0.8 g or less, further more preferably 0.5 g or less, even more preferably 0.4 g or less, based on 1 g of hair.

The water content of wet hair can be calculated from a difference between the mass of wet hair and the mass of hair in a dry state (hereinafter, referred to a dry mass). The dry mass of hair is a mass of hair left to stand for 24 hours in a state of being suspended in a constant-temperature and constant-humidity chamber (temperature: 25° C. and humidity: 60% RH).

Step 2

The step 2 is a step of performing hair treatment with a hair treatment agent shown below on the hair subjected to hair dyeing in the step 1. This ensures that the color of dyed hair obtained by the hair dyeing in the step 1 can be made more vivid and the thus-obtained color can be maintained. The step 2 may be implemented successively to the step 1 (i.e. immediately after the step 1), or may be implemented after the elapse of a certain time period (e.g. several hours to several weeks) after the step 1 as long as the color of dyed hair remains during the time period. From the viewpoint of making the color of dyed hair more vivid and maintaining the thus-obtained color, it is preferable to implement the step 2 successively to the step 1.

From the viewpoint of improving the uniform application properties to hair and enhancing the vividness of the color of dyed hair, the amount of a hair treatment agent applied to the hair dyed in the step 1 is preferably 0.001 or more, more preferably 0.005 or more, further more preferably 0.01 or more, and preferably 100 or less, more preferably 10 or less, further more preferably 1 or less, in terms of bath ratio to the dry mass of hair (mass of the hair cosmetic composition/dry mass of hair).

The hair treatment agent may be applied to the hair using, for example, a comb, a brush or fingers, and may be applied to the entirety or a part of the hair.

After the hair treatment agent is applied to the hair, the hair may be rinsed off or dried without being rinsed off. For more reliably exhibiting the vividness of the color of dyed hair, it is preferable that the hair treatment agent be dried without being rinsed off after the hair treatment agent is applied to the hair. From the viewpoint of reducing the treatment time while exhibiting the vividness of the color of dyed hair, the drying can be performed preferably after the hair is left to stand for 10 minutes or less, more preferably 5 minutes or less, further more preferably less than 5 minutes, further more preferably less than 2 minutes, further more preferably 1 minute or less the hair treatment agent is applied to the hair, even more preferably immediately after the hair treatment agent is applied to the hair.

When the hair to which the hair treatment agent has been applied is dried, it is preferable that the drying be performed at a temperature higher than 40° C., more preferably at 45° C. or higher and 220° C. or lower, from the viewpoint of shortening the treatment time, suppressing damage to the hair and more reliably exhibiting the vividness of the color of dyed hair. The drying step may include not only application of heat to the hair, but also application of a physical force such as air flow to the hair, or combing of the hair with a comb, a brush or a finger. The drying step can be implemented with a hood dryer, a hair dryer, a hair iron, Climazon or the like. When the drying step is implemented with a hood dryer or a hair dryer, the drying temperature is preferably 40° C. or higher and 110° C. or lower, more preferably 50° C. or higher and 90° C. or lower. When the drying step is implemented with a hair iron, the drying temperature is preferably 110° C. or higher and 220° C. or lower, more preferably 140° C. or higher and 200° C. or lower.

The epoxy-aminosilane copolymer as a component (A) is capable of self-crosslinking in the drying process after application to the hair, and therefore does not require an electromagnetic radiation for crosslinking. Therefore, in order to simplify the treatment, it is preferable that step 2 should not include a step of exposing the hair to which a hair treatment agent has been applied to an electromagnetic radiation with an apparatus for supplying an electromagnetic radiation. The present invention aims to quickly enhance the vividness of the color of hair after hair dyeing rather than to reshape the hair, and therefore for simplification of the treatment, it is preferable that the step 2 should not include a step of mechanically reshaping the hair.

Hereinafter, details of the hair treatment agent which is used in the method for treating hair according to the present invention will be described.

[Component (A): Epoxy-Aminosilane Copolymer]

The epoxy-aminosilane copolymer as the component (A) is a reaction product of compounds (a) to (d) shown below.

<Compounds (a) and (b)>

The compound (a) is a polysiloxane containing at least two oxiranyl groups or oxetanyl groups, and examples thereof include polysiloxanes of formula (1) below:

(1)

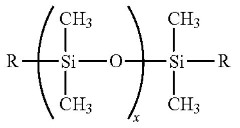

wherein R represents a hydrocarbon group having 1 to 6 carbon atoms and an oxiranyl group or an oxetanyl group at the end thereof and optionally containing a hetero atom, and x represents a number of 1 to 1,000.

The compound (b) is a polyether containing at least two oxiranyl groups or oxetanyl groups, and examples thereof include polyethers of formula (2) below:

(2)

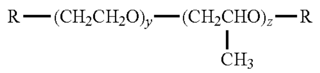

wherein R represents the same meaning as described above, and y represents a number of 1 to 100 and z represents a number of 0 to 100 where y+z equals 1 to 200.

In formulae (1) and (2), the hetero atom optionally contained in R is preferably an oxygen atom. Examples of R include an oxiranylmethyl group (glycidyl group), an oxiranylmethoxy group (glycidyloxy group), an oxiranylmethoxypropyl group (glycidyloxypropyl group), an oxetanylmethyl group, an oxetanylmethoxy group, an oxetanylmethoxypropyl group and a 3-ethyloxetanylmethyl group. Among them, hydrocarbon groups having 1 to 4 carbon atoms and an oxiranyl group and optionally containing a hetero oxygen atom are preferable, and at least one selected from the group consisting of an oxiranylmethyl group (glycidyl group), an oxiranylmethoxy group (glycidyloxy group) and an oxiranylmethoxypropyl group (glycidyloxypropyl group) is more preferable.

<Compound (c)>

The compound (c) is an aminopropyltrialkoxysilane. Examples of the alkoxy group in the compound (c) include those having 1 to 6 carbon atoms, and those having 2 to 4 carbon atoms, particularly those having 3 carbon atoms are preferable. Among them, an isopropoxy group is preferable. Examples of the compound (c) include aminopropyltrimethoxysilane, aminopropyltriethoxysilane, aminopropyltripropoxysilane, aminopropyltriisopropoxysilane, aminopropyltributoxysilane and aminopropyltri-tert-butoxysilane, and among them, aminopropyltriisopropoxysilane is preferable. The compound (C) can be used alone, or in combination of two or more thereof.

<Compound (d)>

The compound (d) is a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminoethyldimethylamine, aminoethyldiethylamine, aminoethyldibutylamine, aminopropyldimethylamine, aminopropyldiethylamine, aminopropyldibutylamine, benzylamine, naphthylamine, 3-amino-9-ethylcarbazole, 1-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine.

Among them, primary amines are preferable, and one selected from the group consisting of aminopropyldiethylamine, aminopropyldimethylamine and aminopropyldibutylamine is more preferable. The compound (d) can be used alone, or in combination of two or more thereof.

The compounds (a) to (d) are reacted by, for example, circulating the compounds in a solvent such as isopropanol for a certain amount of time. Here, the molar ratio of oxiranyl groups or oxetanyl groups in the compounds (a) and (b) to the amino group in the compound (c) is preferably 1 or more, more preferably 1.1 or more, further more preferably 1.2 or more, and preferably 4 or less, more preferably 3.9 or less, further more preferably 3.8 or less.

Examples of the component (A) include those named polysilicone-29 in INCI, and examples of the marketed products thereof include Silsoft CLX-E manufactured by Momentive Performance Materials Inc. (active ingredient content: 15 mass %; containing dipropylene glycol and water).

From the viewpoint of enhancing the vividness of the color of hair and the hair washing resistance, the content of the component (A) in the hair treatment agent is preferably 0.1 mass % or more, more preferably 0.2 mass % or more, further more preferably 0.5 mass % or more, even more preferably 0.8 mass % or more, and preferably 5 mass % or less, more preferably 3 mass % or less, further more preferably 2 mass % or less, even more preferably 1.5 mass % or less. From the above viewpoint, the specific range of the content of the component (A) in the hair treatment agent is preferably from 0.1 mass % to 5 mass %, more preferably from 0.2 mass % to 3 mass %, further more preferably from 0.5 mass % to 2 mass %, even more preferably from 0.8 mass % to 1.5 mass %.

[Component (B): Water]

The content of water as a component (B) in the hair treatment agent is preferably 10 mass % or more, more preferably 15 mass % or more, further more preferably 20 mass % or more, from the viewpoint of facilitating application to the hair, and preferably 99 mass % or less, more preferably 85 mass % or less, further more preferably 80 mass % or less, from the viewpoint of facilitating drying of hair after the hair treatment agent is applied. From the above viewpoints, the content of the component (B) in the hair treatment agent is preferably from 10 mass % to 99 mass %, more preferably from 15 mass % to 85 mass %, further more preferably from 20 mass % to 80 mass %.

[pH]

The pH of the hair treatment agent is adjusted to be in an acidic range or a basic range from the viewpoint of enhancing the reaction rate of a trialkoxysilane moiety of the component (A) and enhancing the vividness of the color of hair and the hair washing resistance.

When the hair treatment agent is in an acidic range, the pH thereof is 4.0 or less, preferably 3.8 or less, more preferably 3.5 or less, and preferably 1.0 or more, more preferably 1.5 or more, further more preferably 2.0 or more, even more preferably 2.5 or more, from the viewpoint of enhancing the reaction rate of the trialkoxysilane moiety of the component (A) in the acidic range and enhancing the vividness of the color of hair and the hair washing resistance. From the above viewpoint, the specific range of the pH when the hair treatment agent is in the acidic range is preferably from 1.0 to 4.0, more preferably from 1.5 to 3.8, further more preferably from 2.0 to 3.5, even more preferably from 2.5 to 3.5.

The pH is a value measured at 25° C. Specifically, the pH can be measured by a method described in Examples.

Meanwhile, when the hair treatment agent is in a basic range, the pH thereof is 8.0 or more, preferably 8.5 or more, and preferably 12 or less, more preferably 11 or less, further more preferably 10 or less, from the viewpoint of enhancing the reaction rate of the trialkoxysilane moiety of the component (A) in the basic range and enhancing the vividness of the color of hair and the hair washing resistance. From the above viewpoint, the specific range of the pH when the hair treatment agent is in the basic range is preferably from 8.0 to 12, more preferably from 8.0 to 11, further more preferably from 8.5 to 10.

[Component (C): pH Adjuster]

The hair treatment agent contains a pH adjuster as a component (C) for adjusting the pH of the hair treatment agent to be in an acidic range or a basic range.

From the viewpoint of enhancing the vividness of the color of hair and the hair washing resistance, the content of the component (C) in the hair treatment agent is preferably 0.05 mass % or more, and preferably 15 mass % or less, more preferably 10 mass % or less. From the above viewpoint, the specific range of the content of the component (C) in the hair treatment agent is preferably from 0.05 mass % to 15 mass %, more preferably from 0.05 mass % to 10 mass %.

When the pH of the hair treatment agent is 4 or less, it is preferable that the hair treatment agent contain the following component (C1) as the component (C).

(C1) One or More Selected from the Group Consisting of Phosphoric Acid and Organic Acids The organic acid is preferably an organic acid having 10 or less carbon atoms, and examples thereof include acids having a short-chain alkyl group having 10 or less carbon atoms, such as alkylphosphoric acids, alkylsulfonic acids and alkylsulfuric acids; acidic amino acids such as L-glutamic acid and L-aspartic acid; pyroglutamic acid; aromatic acids such as benzoic acid and p-toluenesulfonic acid; hydroxy acids such as monohydroxycarboxylic acids such as glycolic acid, lactic acid and glyceric acid, hydroxydicarboxylic acids such as malic acid and tartaric acid, and hydroxytricarboxylic acids such as citric acid; and dicarboxylic acids such as oxalic acid, malonic acid, maleic acid and succinic acid. From the viewpoint of enhancing the vividness of the color of hair and the hair washing resistance, the component (C1) is preferably one or more selected from the group consisting of phosphoric acid, hydroxy acids and dicarboxylic acids, more preferably one or more selected from the group consisting of phosphoric acid, aliphatic α-hydroxy acids having 2 to 8 carbon atoms and aliphatic dicarboxylic acids having 2 to 8 carbon atoms, further more preferably aliphatic α-hydroxy acids having 2 to 8 carbon atoms. Of these, one or more selected from the group consisting of phosphoric acid, succinic acid, lactic acid, malic acid and citric acid are preferable, and one or more selected from the group consisting of lactic acid, malic acid and citric acid are more preferable.

From the viewpoint of enhancing the vividness of the color of hair and the hair washing resistance, the content of the component (C1) in the hair treatment agent is preferably 0.05 mass % or more, more preferably 0.1 mass % or more, further more preferably 0.2 mass % or more, even more preferably 0.5 mass % or more, and preferably 15 mass % or less, more preferably 10 mass % or less, further more preferably 8 mass % or less, further more preferably 5 mass % or less, even more preferably 3 mass % or less. From the above viewpoint, the specific range of the content of the component (C1) in the hair treatment agent is preferably from 0.05 mass % to 15 mass %, more preferably from 0.05 mass % to 10 mass %, further more preferably from 0.1 mass % to 10 mass %, further more preferably from 0.2 mass % to 8 mass %, further more preferably from 0.5 mass % to 5 mass %, even more preferably from 0.5 mass % to 3 mass %.

When the pH of the hair treatment agent is 8 or more, it is preferable that the hair treatment agent contain the following component (C2) as the component (C).

(C2) One or More Selected from the Group Consisting of Ammonia, Alkanolamines, Silicates, Phosphates, Carbonates and Borates Examples of the alkanolamine include monoethanolamine, isopropanolamine, 2-amino-2-methylpropanol, 2-aminobutanol and tris(hydroxymethyl)aminomethane, examples of the silicate include sodium orthosilicate, sodium metasilicate and sodium sesquisilicate, examples of the phosphate include trisodium phosphate, examples of the carbonate include disodium carbonate, sodium hydrogen carbonate, dipotassium carbonate and potassium hydrogen carbonate, and examples of the borate include sodium borate. As these salts, one or more selected from the group consisting of ammonia, alkali metals and alkali earth metals can be used. From the viewpoint of enhancing the vividness of the color of hair and the hair washing resistance, the component (C2) is preferably one or more selected from the group consisting of ammonia, alkanolamines and carbonates, more preferably one or more selected from the group consisting of ammonia and alkanolamines, further more preferably an alkanolamine. Of these, one or more selected from the group consisting of monoethanolamine, isopropanolamine, 2-amino-2-methylpropanol and tris(hydroxymethyl)aminomethane are preferable, and one or more selected from the group consisting of monoethanolamine, 2-amino-2-methylpropanol and tris(hydroxymethyl)aminomethane are more preferable.

From the viewpoint of enhancing the vividness of the color of hair and the hair washing resistance, the content of the component (C2) in the hair treatment agent is preferably 0.05 mass % or more, more preferably 0.1 mass % or more, further more preferably 0.15 mass % or more, and preferably 10 mass % or less, more preferably 8 mass % or less, further more preferably 5 mass % or less, further more preferably 3 mass % or less, further more preferably 1.5 mass % or less, even more preferably 0.8 mass % or less. From the above viewpoint, the specific range of the content of the component (C2) in the hair treatment agent is preferably from 0.05 mass % to 10 mass %, more preferably from 0.05 mass % to 8 mass %, further more preferably from 0.05 mass % to 5 mass %, further more preferably from 0.1 mass % to 3 mass %, further more preferably from 0.15 mass % to 1.5 mass %, even more preferably from 0.15 mass % to 0.8 mass %.

From the viewpoint of enhancing the vividness of the color of hair and the hair washing resistance, a mass ratio of the component (C) to the component (A), (C)/(A), is preferably 0.05 or more, and preferably 15 or less, more preferably 10 or less. From the above viewpoint, the specific range of the mass ratio (C)/(A) is preferably from 0.05 to 15, more preferably from 0.05 to 10.

When the pH of the hair treatment agent is 4 or less, a mass ratio (C1)/(A) is preferably 0.05 or more, more preferably 0.1 or more, further more preferably 0.15 or more, further more preferably 0.2 or more, even more preferably 0.5 or more, and preferably 15 or less, more preferably 10 or less, further more preferably 8 or less, further more preferably 7 or less, further more preferably 5 or less, even more preferably 3 or less, from the above viewpoint. From the above viewpoint, the specific range of the mass ratio (C1)/(A) is preferably from 0.05 to 15, more preferably from 0.05 to 10, further more preferably from 0.1 to 10, further more preferably from 0.1 to 8, further more preferably from 0.15 to 7, further more preferably from 0.2 to 7, further more preferably from 0.5 to 7, further more preferably from 0.5 to 5, even more preferably from 0.5 to 3.

When the pH of the hair treatment agent is 8 or more, a mass ratio (C2)/(A) is preferably 0.05 or more, more preferably 0.1 or more, further more preferably 0.15 or more, and preferably 10 or less, more preferably 8 or less, further more preferably 5 or less, further more preferably 3 or less, further more preferably 1.5 or less, even more preferably 0.8 or less, from the above viewpoint. From the above viewpoint, the specific range of the mass ratio (C2)/(A) is preferably from 0.05 to 10, more preferably from 0.05 to 8, further more preferably from 0.05 to 5, further more preferably from 0.1 to 3, further more preferably from 0.15 to 1.5, even more preferably from 0.15 to 0.8.

[Component (D): Organic Solvent]

The hair treatment agent may contain an organic solvent as a component (D). From the viewpoint of enhancing the vividness of the color of hair, examples of the organic solvent include lower alkanols such as ethanol, 1-propanol, 2-propanol, 1-butanol and 2-butanol; polyhydric alcohols such as methylpropanediol, pentylene glycol, hexylene glycol, octanediol, decanediol and triethylene glycol; aromatic alcohols such as benzyl alcohol, cinnamyl alcohol, phenethyl alcohol, p-anisyl alcohol, p-methylbenzyl alcohol, phenoxyethanol, 2-benzyloxyethanol and phenylpropanol; ether alcohols such as ethylene glycol monoethyl ether, ethylene glycol monobutyl ether, diethylene glycol monomethyl ether, diethylene glycol monoethyl ether, diethylene glycol monobutyl ether and ethylhexyl glyceryl ether; alkyl ethers such as dimethyl ether; N-alkylpyrrolidones such as N-methylpyrrolidone, N-ethylpyrrolidone and N-(2-hydroxyethyl)-2-pyrrolidone; cyclic esters such as γ-valerolactone, γ-caprolactone, γ-crotonolactone and γ-butyrolactone; and acyclic esters such as diisostearyl malate, octyldodecyl lactate, ethyl lactate, butyl lactate, isononyl isononanoate, isotridecyl isononanoate, octyldodecyl myristate, isopropyl palmitate, isopropyl isostearate, butyl stearate, myristyl myristate, isopropyl myristate, octyldodecyl myristate, neopentyl glycol dicaprate, tricaproin and pentaerythrityl 2-ethylhexanoate. Among them, linear alcohols having 1 to 4 carbon atoms and aromatic alcohols are preferable, ethanol, benzyl alcohol, phenoxyethanol and phenethyl alcohol are more preferable, and ethanol is further more preferable, from the viewpoint of enhancing the vividness of the color of hair and the hair washing resistance.

The component (D) can be used alone, or in combination of two or more thereof. From the viewpoint of enhancing the vividness of the color of hair and the hair washing resistance, the content of the component (D) in the hair treatment agent is preferably 1 mass % or more, more preferably 4 mass % or more, further more preferably 8 mass % or more, and preferably 45 mass % or less, more preferably 35 mass % or less, further more preferably 30 mass % or less. From the above viewpoint, the specific range of the content of the component (D) in the hair treatment agent is preferably from 1 mass % to 45 mass %, more preferably from 4 mass % to 35 mass %, further more preferably from 8 mass % to 30 mass %.

[Component (E): Water-Soluble Thickening Polymer]

The hair treatment agent may contain a water-soluble thickening polymer. Examples of the water-soluble thickening polymer include anionic thickening polymers, cationic thickening polymers and nonionic thickening polymers.

Specific examples of the anionic thickening polymer include polyacrylic acids (Noveon Inc.: CARBOPOLs 941 and 981), acrylic acid-alkyl methacrylate copolymers (Noveon Inc.: CARBOPOL ETD 2020), hydrolysates of polymers obtained by partially crosslinking a lower alkyl vinyl ether/maleic anhydride copolymer with a terminally unsaturated diene compound, or monoalkyl esters thereof (ASHLAND Inc.: STABILIZEs 06 and QM), carrageenan (e.g. MITSUBISHI RAYON CO., LTD.: SOAGEENAs LX22 and ML210), xanthan gum (e.g. Sumitomo Dainippon Pharma Co., Ltd.: ECHO GUM T), welan Gum (e.g. Sansho Co., Ltd.: K1C376 and K1A96), hydroxypropylxanthan gum (e.g. Sumitomo Dainippon Pharma Co., Ltd.: RHABALL GUM EX), sodium stearoxy PG-hydroxyethylcellulose sulfonate, and hydroxyethyl acrylate/sodium acryloyldimethyl taurate copolymers (e.g. SEPPIC Inc.: SIMULGEL NS and SEPINOV EMT10).

Examples of the cationic thickening polymer include natural or semisynthetic cationic polysaccharides, and synthetic polymers containing an amino group or an ammonium group on the side chain of the polymer chain, or containing a diallyl quaternary ammonium salt as a constituent unit.

Specific examples of the cationic polysaccharide include cationized cellulose derivatives (e.g. Lion Corporation: LEOGARDs G and GP, The Dow Chemical Company: UCARE POLYMERs JR-125, JR-400, JR-30M, LR-400 and LR-30M, and Akzo Nobel N.V.: CELQUATs H-100 and L-200), cationized guar gum derivatives (e.g. Solvay S.A.: JAGUARs C-13S and C-17, and DSP GOKYO FOOD & CHEMICAL Co., Ltd.: RHABALL GUMS CG-M, CG-M7 and CG-M8M), hydroxypropylchitosan (e.g. ICHIMARU PHARCOS Co., Ltd.: CHITIN Liquid-HV-10), and chitosan dl-pyrrolidone carboxylic acid salts (e.g. Union carbide Corporation: KYTAMER PC).

Examples of the synthetic cationic polymer containing an amino group or an ammonium group on the side chain of the polymer chain include synthetic cationic polymers containing a trialkylaminoalkyl (meth)acrylate, a trialkylaminoalkyl (meth)acrylamide, a (meth)acrylamide, a vinylamine or the like as a constituent unit, and specific examples thereof include (acrylic acid/methyl acrylate/3-methacryloylaminopropyltrimethylammonium chloride) copolymers (INCI name: polyquaternium-47, e.g. Lubrizol Corp.: MERQUAT 2201), (acrylic acid/acrylamide/methylmethacrylamidopropyltrimethylammonium chloride) copolymers (INCI name: polyquaternium-53, e.g. Lubrizol Corp.: MERQUAT 2003), (dimethylacrylamide/ethyltrimonium chloride methacrylate) copolymers (e.g. BASF SE: Tinobis CD), and (vinylamine/vinyl alcohol) copolymers (e.g. Sekisui Specialty Chemicals Co., Ltd.: SEVOL ULTALUX AD, and Mitsubishi Chemical Corporation: Diafix C-601).

Specific examples of the synthetic cationic polymer containing a diallyl quaternary ammonium salt as a constituent unit include polymers of diallyldimethylammonium chloride (INCI name: polyquaternium-6, e.g. Lubrizol Corp.: MERQUAT 100), (dimethyldiallylammonium chloride/acrylamide) copolymers (INCI name: polyquaternium-7, e.g. Lubrizol Corp.: MERQUATs 550 and 740), (acrylic acid/diallyldimethylammonium chloride) copolymers (INCI name: polyquaternium-22, e.g. Lubrizol Corp.: MERQUATs 280 and 295), and (acrylamide/acrylic acid/diallyldimethylammonium chloride) copolymers (INCI name: polyquaternium-39, e.g. Lubrizol Corp.: MERQUAT PLUSs 3330 and 3331).

Examples of the nonionic thickening polymer include natural or semisynthetic nonionic polysaccharides, and synthetic nonionic polymers containing a vinyl alcohol or an oxyalkylene as a constituent unit.

Specific examples of the natural or semisynthetic nonionic polysaccharide include water-soluble natural polysaccharides such as starch, guar gum, locust bean gum and glucomannan; and water-soluble hydroxyalkylated polysaccharides obtained by reacting an alkylene oxide with cellulose, starch, guar gum, locust bean gum or the like. Specific examples thereof include guar gum (e.g. DSP GOKYO FOOD & CHEMICAL Co., Ltd.: FIBERON S), pullulan (e.g. HAYASHIBARA CO., LTD.: PULLULAN PI-20), hydroxyethylcellulose (e.g. Daicel FineChem Ltd.: SE-850, and The Dow Chemical Company: CELLOSIZE HEC QP-52000-H), methylhydroxyethylcellulose (Akzo Nobel N.V.: STRUCTURE CELL 12000M), hydroxypropylcellulose (e.g. Nippon Soda Co., Ltd.: HPC-H, HPC-M and HPC-L), and hydroxypropylmethylcellulose (e.g. Shin-Etsu Chemical Co., Ltd.: METOLOSE 60SH-10000).

Specific examples of the synthetic nonionic thickening polymer containing a vinyl alcohol or an oxyalkylene as a constituent unit include polyvinyl alcohols (e.g. The Nippon Synthetic Chemical Industry Co., Ltd.: GOHSENOLs EG-40, GH-05, KH-20 and NH-26), polyethylene glycols with a high degree of polymerization (e.g. The Dow Chemical Company: POLYOXs WSR N-60K, WSR 301 and WDR 303), and (PEG-240/Decyltetradeceth-20/HDI) copolymers (e.g. ADEKA CORPORATION: ADEKANOL GT-700).

These water-soluble thickening polymers can be used alone, or in combination of two or more thereof. From the viewpoint of enhancing the vividness of the color of hair and developing the hair washing resistance, the content of the water-soluble thickening polymer in the hair treatment agent is preferably 0.8 mass % or less, more preferably 0.5 mass % or less, further more preferably 0.2 mass % or less, and preferably 0.01 mass % or more, more preferably 0.05 mass % or more. From the above viewpoint, the specific range of the content of the water-soluble thickening polymer in the hair treatment agent is preferably from 0 mass % to 0.8 mass %, more preferably from 0.01 mass % to 0.8 mass %, further more preferably from 0.01 mass % to 0.5 mass %, even more preferably from 0.05 mass % to 0.2 mass %.

[Optional Components]

In addition to the above components, the hair treatment agent may further approximately contain components which are normally blended in hair cosmetic compositions. Examples thereof include anti-dandruff agents; vitamin preparations; fungicides; anti-inflammatory agents; antiseptic agents; chelating agents; humectants; coloring agents such as dyes and pigments; essences; pearl ingredients; perfumes; ultraviolet absorbers; antioxidant agents; photocatalysts; shea butter; rose water; sunflower seed oil; orange oil; and eucalyptus oil.

[Dosage Form]

The dosage form of the hair treatment agent can be, for example, a liquid, a milky liquid, a cream, a gel, a paste, a mousse, an aerosol or the like, and is preferably a liquid, a gel, a paste, a mousse or an aerosol. When an aerosol is employed, contents of each component as described hereinbefore are those in a stock solution except a propellant, and the pH of the hair treatment agent is that of the stock solution except a propellant.

Hair Treatment Kit

The present invention also encompasses an aspect of a hair treatment kit obtained by combining the hair treatment agent with the hair dye composition described above.

As the hair dye composition, all types of hair dye compositions can be used such as one-part hair dye compositions containing a dye directly and two-part hair dye compositions containing a first agent containing an alkali agent and an oxidation dye precursor and a second agent containing an oxidizing agent as in the case of the hair dye composition used in the step 1 described above. The form of the hair dye composition may be any of a cream, a liquid, a foam and the like.

From the viewpoint of more readily enhancing the vividness of the color of hair after hair dyeing, the hair dye composition is preferably a semipermanent hair dye material or a permanent hair dye capable of dyeing the inside of hair, more preferably a permanent hair dye, rather than a temporary hair dye material which covers the hair with a film agent or the like.

Post-Hair-Dyeing Treatment Agent and Method for Enhancing Chroma of Color of Dyed Hair The present invention also encompasses an aspect of the hair treatment agent as a post-hair-dyeing treatment agent, and an aspect of a method for enhancing the chroma of the color of dyed hair, containing implementing the step 2 above on hair after hair dyeing. The preferred hair dyeing treatment in these aspects is the same as described above.

In these cases, an object to be treated with the post-hair-dyeing treatment agent, or an object to be subjected to the step 2 in the method for enhancing the chroma of the color of dyed hair may be hair subjected to hair dyeing, and is not limited to dyed hair immediately after hair dyeing. That is, the post-treatment with the post-hair-dyeing treatment agent or the step 2 in the method for enhancing the chroma of the color of dyed hair may be implemented successively to the hair dyeing in the step 1, or may be implemented after the elapse of a certain time period (e.g. several hours to several weeks) after the hair dyeing. From the viewpoint of improving the compatibility of the hair treatment agent with hair to obtain good uniform application properties, it is preferable to implement the step 2 on hair brought into a state of wet hair by appropriately performing washing with shampoo, rinsing and the like in advance. In particular, from the viewpoint of making the color of dyed hair more vivid and maintaining the thus-obtained color, it is preferable to implement the step 2 successively to the step 1.

With respect to the embodiments described above, preferred aspects of the present invention are further described below.

<1> A method for treating hair, comprising steps 1 and 2 below:

(step 1) applying a hair dye composition to hair to dye the hair; and (step 2) applying a hair treatment agent to the hair subjected to hair dyeing in the step 1, the hair treatment agent having a pH of 4 or less or 8 or more and comprising the following components (A), (B) and (C):

(A) an epoxy-aminosilane copolymer which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3 amino-9-ethylcarbazole, 1-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine;

(B) water; and (C) a pH adjuster.

<2> A method for treating hair, comprising steps 1 and 2 below:

(step 1) applying a hair dye composition to hair to dye the hair; and (step 2) applying a hair treatment agent to the hair after the hair dyeing successively to the step 1, the hair treatment agent having a pH of 4 or less or 8 or more and comprising the following components (A), (B) and (C):

(A) an epoxy-aminosilane copolymer which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3-amino-9-ethylcarbazole, I-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine;

(B) water; and (C) a pH adjuster.

<3> The method for treating hair according to <1> or <2>, wherein the compound (a) is preferably a compound of formula (1) below:

(1)

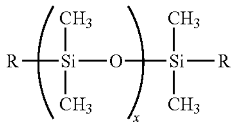

wherein R represents a hydrocarbon group having 1 to 6 carbon atoms and an oxiranyl group or an oxetanyl group at the end thereof and optionally containing a hetero oxygen atom, and x represents a number of 1 to 1,000.

<4> The method for treating hair according to any one of <1> to <3>, wherein the compound (b) is preferably a compound of general formula (2) below:

(2)

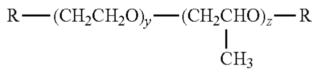

wherein R represents the same meaning as described above, and y represents a number of 1 to 100 and z represents a number of 0 to 100 where y+z equals 1 to 200.

<5> The method for treating hair according to any one of <1> to <4>, wherein R is preferably at least one selected from the group consisting of an oxiranylmethyl group (glycidyl group), an oxiranylmethoxy group (glycidyloxy group), an oxiranylmethoxypropyl group (glycidyloxypropyl group), an oxetanylmethyl group, an oxetanylmethoxy group, an oxetanylmethoxypropyl group and a 3-ethyloxetanylmethyl group, more preferably at least one selected from the group consisting of an oxiranylmethyl group (glycidyl group), an oxiranylmethoxy group (glycidyloxy group) and an oxiranylmethoxypropyl group (glycidyloxypropyl group).

<6> The method for treating hair according to any one of <1> to <5>, wherein the alkoxy group in the compound (c) is preferably one having 1 to 6 carbon atoms, more preferably one having 2 to 4 carbon atoms, further more preferably one having 3 carbon atoms, even more preferably an isopropoxy group.

<7> The method for treating hair according to any one of <1> to <6>, wherein the compound (c) is preferably a compound selected from the group consisting of aminopropyltrimethoxysilane, aminopropyltriethoxysilane, aminopropyltripropoxysilane, aminopropyltriisopropoxysilane, aminopropyltributoxysilane and aminopropyltri-tert-butoxysilane, more preferably aminopropyltriisopropoxysilane.

<8> The method for treating hair according to any one of <1> to <7>, wherein the compound (d) is preferably a primary amine, more preferably one selected from the group consisting of aminopropyldiethylamine, aminopropyldimethylamine and aminopropyldibutylamine.

<9> The method for treating hair according to any one of <1> to <8>, wherein the component (A) is preferably polysilicone-29.

<10> The method for treating hair according to any one of <1> to <9>, wherein a mass ratio of the component (C) to the component (A), (C)/(A), is preferably from 0.05 to 15.

<11> The method for treating hair according to any one of <1> to <10>, wherein the hair treatment agent has a pH of 4 or less, and preferably comprises (C1) one or more selected from the group consisting of phosphoric acid and organic acids as the component (C).

<12> The method for treating hair according to <11>, wherein the component (C1) is one or more selected from the group consisting of phosphoric acid, succinic acid, lactic acid, malic acid and citric acid, more preferably one or more selected from the group consisting of lactic acid, malic acid and citric acid.

<13> The method for treating hair according to <11> or <12>, wherein a mass ratio of the component (C1) to the component (A), (C1)/(A), is preferably 0.05 or more, more preferably 0.1 or more, further more preferably 0.2 or more, even more preferably 0.5 or more, and preferably 15 or less, more preferably 10 or less, further more preferably 8 or less, further more preferably 5 or less, even more preferably 3 or less.

<14> The method for treating hair according to any one of <1> to <10>, wherein the hair treatment agent has a pH of 8 or more, and preferably comprises (C2) one or more selected from the group consisting of ammonia, alkanolamines, silicates, phosphates, carbonates and borates as the component (C).

<15> The method for treating hair according to <14>, wherein the component (C2) is preferably one or more selected from the group consisting of ammonia, alkanolamines and carbonates, more preferably one or more selected from ammonia and alkanolamines, further more preferably an alkanolamine, even more preferably one or more selected from the group consisting of monoethanolamine, isopropanolamine, 2-amino-2-methylpropanol and tris(hydroxymethyl)aminomethane, further more preferably one or more selected from the group consisting of monoethanolamine, 2-amino-2-methylpropanol and tris(hydroxymethyl)aminomethane.

<16> The method for treating hair according to <14> or <15>, wherein a mass ratio of the component (C2) to the component (A), (C2)/(A), is preferably 0.05 or more, more preferably 0.1 or more, further more preferably 0.15 or more, and preferably 10 or less, more preferably 8 or less, further more preferably 5 or less, further more preferably 3 or less, even more preferably 1.5 or less, even more preferably 0.8 or less.

<17> A method for treating hair, comprising steps 1 and 2 below:

(step 1) applying a hair dye composition to hair to dye the hair; and (step 2) applying a hair treatment agent to the hair subjected to hair dyeing in the step 1, the hair treatment agent having a pH of 1 to 4 and comprising the following components (A), (B) and (C1), wherein a mass ratio of the component (C1) to the component (A), (C1)/(A), is from 0.1 to 7:

(A) polysilicone-29 at 0.2 to 3 mass %;

(B) water; and (C1) one or more pH adjusters at 0.05 to 10 mass %, with the pH adjusters being selected from the group consisting of phosphoric acid, aliphatic α-hydroxy acids having 2 to 8 carbon atoms and aliphatic dicarboxylic acids having 2 to 8 carbon atoms.

<18> A method for treating hair, comprising steps 1 and 2 below:

(step 1) applying a hair dye composition to hair to dye the hair; and (step 2) applying a hair treatment agent to the hair after the hair dyeing successively to the step 1, the hair treatment agent having a pH of 1 to 4 and comprising the following components (A), (B) and (C1), wherein a mass ratio of the component (C1) to the component (A), (C1)/(A), is from 0.1 to 7:

(A) polysilicone-29 at 0.2 to 3 mass %;

(B) water; and (C1) one or more pH adjusters at 0.05 to 10 mass %, with the pH adjusters being selected from the group consisting of phosphoric acid, aliphatic α-hydroxy acids having 2 to 8 carbon atoms and aliphatic dicarboxylic acids having 2 to 8 carbon atoms.

<19> A method for treating hair, comprising steps 1 and 2 below:

(step 1) applying a hair dye composition to hair to dye the hair; and (step 2) applying a hair treatment agent to the hair subjected to hair dyeing in the step 1, the hair treatment agent having a pH of 2.0 to 3.5 and comprising the following components (A), (B) and (C1), wherein a mass ratio of the component (C1) to the component (A), (C1)/(A), is from 0.5 to 3:

(A) polysilicone-29 at 0.5 to 2 mass %;

(B) water; and (C1) one or more pH adjusters at 0.1 to 10 mass %, with the pH adjusters being selected from the group consisting of phosphoric acid, succinic acid, lactic acid, malic acid and citric acid.

<20> A method for treating hair, comprising steps 1 and 2 below:

(step 1) applying a hair dye composition to hair to dye the hair; and (step 2) applying a hair treatment agent to the hair after the hair dyeing successively to the step 1, the hair treatment agent having a pH of 2.0 to 3.5 and comprising the following components (A), (B) and (C1), wherein a mass ratio of the component (C1) to the component (A), (C1)/(A), is from 0.5 to 3:

(A) polysilicone-29 at 0.5 to 2 mass %;

(B) water; and (C1) one or more pH adjusters at 0.1 to 10 mass %, with the pH adjusters being selected from the group consisting of phosphoric acid, succinic acid, lactic acid, malic acid and citric acid.

<21> A method for treating hair, comprising steps 1 and 2 below:

(step 1) applying a hair dye composition to hair to dye the hair; and (step 2) applying a hair treatment agent to the hair subjected to hair dyeing in the step 1, the hair treatment agent having a pH of 8.0 to 12 and comprising the following components (A), (B) and (C2), wherein a mass ratio of the component (C2) to the component (A), (C2)/(A), is from 0.1 to 3:

(A) polysilicone-29 at 0.2 to 3 mass %;

(B) water; and (C2) one or more pH adjusters at 0.05 to 8 mass %, with the pH adjusters being selected from the group consisting of alkanolamines.

<22> A method for treating hair, comprising steps 1 and 2 below:

(step 1) applying a hair dye composition to hair to dye the hair; and (step 2) applying a hair treatment agent to the hair after hair dyeing successively to the step 1, the hair treatment agent having a pH of 8.0 to 12 and comprising the following components (A), (B) and (C2), wherein a mass ratio of the component (C2) to the component (A), (C2)/(A), is from 0.1 to 3:

(A) polysilicone-29 at 0.2 to 3 mass %;

(B) water; and (C2) one or more pH adjusters at 0.05 to 8 mass %, with the pH adjusters being selected from the group consisting of alkanolamines.

<23> A method for treating hair, comprising steps 1 and 2 below:

(step 1) applying a hair dye composition to hair to dye the hair; and (step 2) applying a hair treatment agent to the hair subjected to hair dyeing in the step 1, the hair treatment agent having a pH of 8.5 to 10 and comprising the following components (A), (B) and (C2), wherein a mass ratio of the component (C2) to the component (A), (C2)/(A), is from 0.15 to 0.8:

(A) polysilicone-29 at 0.5 to 2 mass %;

(B) water; and (C2) one or more pH adjusters at 0.1 to 5 mass %, with the pH adjusters being selected from the group consisting of monoethanolamine, 2-amino-2-methylpropanol and tris(hydroxymethyl)aminomethane.

<24> A method for treating hair, comprising steps 1 and 2 below:

(step 1) applying a hair dye composition to hair to dye the hair; and (step 2) applying a hair treatment agent to the hair after hair dyeing successively to the step 1, the hair treatment agent having a pH of 8.5 to 10 and comprising the following components (A), (B) and (C2), wherein a mass ratio of the component (C2) to the component (A), (C2)/(A), is from 0.15 to 0.8:

(A) polysilicone-29 at 0.5 to 2 mass %;

(B) water; and (C2) one or more pH adjusters at 0.1 to 5 mass %, with the pH adjusters being selected from the group consisting of monoethanolamine, 2-amino-2-methylpropanol and tris(hydroxymethyl)aminomethane.

<25> The method for treating hair according to any one of <1> to <24>, wherein the content of the component (A) in the hair treatment agent is preferably 0.1 mass % or more, more preferably 0.2 mass % or more, further more preferably 0.5 mass % or more, even more preferably 0.8 mass % or more, and preferably 5 mass % or less, more preferably 3 mass % or less, further more preferably 2 mass % or less, even more preferably 1.5 mass % or less.

<26> The method for treating hair according to any one of <1> to <25>, wherein the content of the component (B) in the hair treatment agent is preferably 10 mass % or more, more preferably 15 mass % or more, further more preferably 20 mass % or more, and preferably 99 mass % or less, more preferably 85 mass % or less, further more preferably 80 mass % or less.

<27> The method for treating hair according to <11>, <12>, <13>, <17>, <18>, <19> or <20>, wherein the content of the component (C1) in the hair treatment agent is preferably 0.05 mass % or more, more preferably 0.1 mass % or more, further more preferably 0.2 mass % or more, even more preferably 0.5 mass % or more, and preferably 15 mass % or less, more preferably 10 mass % or less, further more preferably 8 mass % or less, further more preferably 5 mass % or less, even more preferably 3 mass % or less.

<28> The method for treating hair according to <14>, <15>, <16>, <21>, <22>, <23> or <24>, wherein the content of the component (C2) in the hair treatment agent is preferably 0.05 mass % or more, more preferably 0.1 mass % or more, further more preferably 0.15 mass % or more, and preferably 10 mass % or less, more preferably 8 mass % or less, further more preferably 5 mass % or less, further more preferably 3 mass % or less, further more preferably 1.5 mass % or less, even more preferably 0.8 mass % or less.

<29> The method for treating hair according to any one of <1> to <28>, wherein the hair treatment agent preferably comprises an organic solvent as the component (D).

<30> The method for treating hair according to <29>, wherein the component (D) is preferably one or more selected from the group consisting of linear alcohols having 1 to 4 carbon atoms and aromatic alcohols, more preferably one or more selected from the group consisting of ethanol, benzyl alcohol, phenoxyethanol and phenethyl alcohol, further more preferably ethanol.

<31> The method for treating hair according to <29> or <30>, wherein the content of the component (D) in the hair treatment agent is preferably 1 mass % or more, more preferably 4 mass % or more, further more preferably 8 mass % or more, and preferably 40 mass % or less, more preferably 30 mass % or less, further more preferably 25 mass % or less.

<32> The method for treating hair according to any one of <1> to <31>, wherein the step 2 is preferably implemented on wet hair.

<33> The method for treating hair according to any one of <1> to <32>, wherein the amount of the hair treatment agent applied to the hair in the step 2 is preferably 0.001 or more, more preferably 0.005 or more, further more preferably 0.01 or more, and preferably 100 or less, more preferably 10 or less, further more preferably 1 or less, in terms of bath ratio to the dry mass of hair (mass of hair cosmetic composition/dry mass of hair).

<34> The method for treating hair according to any one of <1> to <33>, wherein the hair treatment agent is preferably dried without being rinsed off after being applied to the hair in the step 2.

<35> The method for treating hair according to <34>, wherein the drying is performed preferably after the hair is left to stand for 10 minutes or less, more preferably 5 minutes or less, further more preferably less than 5 minutes, further more preferably less than 2 minutes, further more preferably 1 minute or less after the hair treatment agent is applied to the hair, even more preferably immediately after the hair treatment agent is applied to the hair.

<36> The method for treating hair according to <34> or <35>, wherein the drying is performed preferably at a temperature higher than 40° C., more preferably at a temperature of 45° C. or higher and 220° C. or lower.

<37> The method for treating hair according to any one of <1> to <36>, wherein the hair dye composition is a semi-permanent hair dye material or a permanent hair dye, preferably a permanent hair dye.

<38> The method for treating hair according to any one of <1> to <37>, wherein the step 2 preferably does not include either exposing the hair to an electromagnetic radiation with an apparatus for supplying an electromagnetic radiation or mechanically reshaping the hair.

<39> A hair treatment kit comprising: a hair dye composition; and a hair treatment agent having a pH of 4 or less or 8 or more and comprising the following components (A), (B) and (C):

(A) an epoxy-aminosilane copolymer which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3-amino-9-ethylcarbazole, 1-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine;

(B) water; and (C) a pH adjuster.

<40> The hair treatment kit according to <39>, wherein the hair dye composition is a semipermanent hair dye material or a permanent hair dye, preferably a permanent hair dye.

<41> A post-hair-dyeing treatment agent having a pH of 4 or less or 8 or more and comprising the following components (A), (B) and (C):

(A) an epoxy-aminosilane copolymer which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3-amino-9-ethylcarbazole, 1-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine;

(B) water; and (C) a pH adjuster.

<42> A method for enhancing the chroma of the color of dyed hair, comprising implementing the step 2 on hair after hair dyeing:

(step 2) applying a hair treatment agent to hair after hair dyeing, the hair treatment agent having a pH of 4 or less or 8 or more and comprising the following components (A), (B) and (C):

(A) an epoxy-aminosilane copolymer which is a reaction product of the following compounds (a) to (d):

(a) a polysiloxane having at least two oxiranyl groups or oxetanyl groups;

(b) a polyether having at least two oxiranyl groups or oxetanyl groups;

(c) an aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3 amino-9-ethylcarbazole, 1-aminoheptafluorohexane and 2,2,3,3,4,4,5,5,6,6,7,7,8,8,8-pentadecafluoro-1-octaneamine; and secondary amines: methylethylamine, methyloctadecylamine, diethanolamine, dibenzylamine, dihexylamine, dicyclohexylamine, piperidine, pyrrolidine, phthalimide and polymer amine;

(B) water; and (C) a pH adjuster.

<43> The method for enhancing the chroma of the color of dyed hair according to <42>, wherein the hair dyeing is hair dyeing in which a semipermanent hair dye material or a permanent hair dye is applied to hair to dye the hair, preferably hair dyeing in which a permanent hair dye is applied to dye the hair.

EXAMPLES

Examples 1 to 18 and Comparative Examples 1 to 6

The hair treatment agents shown in Tables 1 and 2 were prepared, and the vividness of the color of hair subjected to hair coloring treatment was evaluated in accordance with the following methods and criteria. Tables 1 and 2 show the results.

<Formulation of Shampoo for Evaluation>

| Component | (mass %) |
|---|---|
| Sodium laureth sulfate | 15.5 |
| Lauramide DEA | 1.5 |
| Sodium benzoate | 0.5 |
| EDTA-2Na | 0.3 |
| Phosphoric acid | amount needed for adjustment to pH 7 |
| Purified water | balance |
| Total | 100.0 |

<Formulation of Conditioner for Evaluation>

| Component | (mass %) |
|---|---|
| Cetearyltrimonium chloride | 1.5 |
| Cetearyl alcohol | 2.5 |
| Propylene glycol | 5.0 |
| Perfume | 0.3 |
| Purified water | balance |
| Total | 100 |

[I: Hair Coloring Treatment]

A commercially available bleaching agent was applied to 1 g of Chinese black hair (manufactured by Beaulax Co., Ltd) at a bath ratio of 3.5:1 (bleaching agent: hair), and the hair was left standing at 40° C. for 40 minutes, then rinsed with water at about 40° C., washed with shampoo for evaluation, rinsed with water, and then dried with a dryer. Subsequently, measurement was performed on the CIE color coordinate system (L*, a*, b* and c*) with a D65 light source using a color-difference meter (Color-Difference Meter CR-400 manufactured by Konica Minolta Sensing, Ltd.), and only hair having a L* value of 22.5 to 25.1 (inclusive), a b* value of 10.0 to 13.3 (inclusive) and a c* value of 12.4 to 15.9 (inclusive) was selected, and used as bleached hair.

A commercially available hair color (a liquid obtained by mixing Topchic Color 6R and a Topchic Color Lotion 6% hydrogen peroxide product (each manufactured by Goldwell Company) at a mass ratio of 1:1 was used as a hair color) was applied to 1 g of the bleached hair at a bath ratio of 1:1 (hair color:hair), and the hair was left standing at 30° C. for 30 minutes, and then rinsed with water at about 40° C. Thereafter, the hair was subjected to washing with shampoo for evaluation and rinsing with water two times. A conditioner for evaluation was then applied, and the hair was then rinsed with water at about 40° C., and wiped with a towel to remove excess water.

[II: Treatment with Hair Treatment Agent]

0.3 g of the hair treatment agent was applied to the wet hair after the hair dyeing (containing 0.4 g of water per g of dry hair), and uniformly spread throughout the hair, and the hair was dried with a dryer. Comparative Example 1 was a control without hair treatment after hair coloring treatment (control). In Comparative Example 2, II: treatment with the same hair treatment agent as in Example 3 was first performed and hair dyeing using the commercially available hair color described in [I: Hair coloring treatment] was then performed on the bleached hair described in [I: Hair coloring treatment] (pretreatment).

[Evaluation on Vividness of Color of Hair (Measurement of Δc*1)]

The color of hair immediately after the hair treatment was measured on the CIE color coordinate system (L*, a*, b* and c*) with a D65 light source using a color-difference meter (Color-Difference Meter CR-400 manufactured by Konica Minolta Sensing, Ltd.). The color of hair of Comparative Example 1 without hair treatment after hair coloring treatment was similarly measured on the CIE color coordinate system (L*, a*, b* and c*). The value of Δc*1 was determined as an index of vividness of the color of hair by the following calculation.

$$\Delta c^*1 = (c^* \text{ value of hair immediately after hair treatment}) - (c^* \text{ value of hair of Comparative Example 1})$$

<Evaluation on Vividness of Color of Hair after Repeated Use of Shampoo (Measurement of Δc*2)>

The hair after the hair treatment was washed with shampoo for evaluation and rinsed with water 14 times. A conditioner for evaluation was then applied, and the hair was then rinsed with water at about 40° C., wiped with a towel to remove excess water, and dried with a dryer. The color of the obtained hair after repeated use of shampoo was measured on the CIE color coordinate system (L*, a*, b* and c*) with a D65 light source using a color-difference meter (Color-Difference Meter CR-400 manufactured by Konica Minolta Sensing, Ltd.). The color of hair of Comparative Example 1 without hair treatment after hair coloring treatment was similarly measured on the CIE color coordinate system (L*, a*, b* and c*) after washing with shampoo was performed 14 times. The value of Δc*2 was determined as an index of vividness of the color of hair after repeated use of shampoo by the following calculation.

$$\Delta c^*2 = (c^* \text{ value of hair after washing with shampoo 14 times after hair treatment}) - (c^* \text{ value after washing of hair of Comparative Example 1 with shampoo 14 times})$$

[pH Measurement]

The pH of the hair treatment agent at 25° C. was measured using a pH meter (F-51 manufactured by HORIBA, Ltd.).

TABLE 1

| | Component (mass %) | Example 1 | 2 | 3 | 4 | 5 | 6 | 7 | 8 | 9 | 10 |
|---|---|---|---|---|---|---|---|---|---|---|---|
| (A) | Epoxy-aminosilane copolymer mixture (*1) | 6.7 | 6.7 | 6.7 | 6.7 | 6.7 | 6.7 | 6.7 | 6.7 | 6.7 | 6.7 |
| (B) | Water | Balance | Balance | Balance | Balance | Balance | Balance | Balance | Balance | Balance | Balance |
| (C1) | Lactic acid | 0.1 | 0.2 | 1 | 5 | 10 | — | — | — | — | 1 |
| | Phosphoric acid | — | — | — | — | — | 1 | — | — | — | — |
| | Malic acid | — | — | — | — | — | — | 1 | — | — | — |
| | Succinic acid | — | — | — | — | — | — | — | 1 | — | — |
| | Citric acid | — | — | — | — | — | — | — | — | 1 | — |
| (D) | Ethanol | — | — | — | — | — | — | — | — | — | — |
| | Benzyl alcohol | — | — | — | — | — | — | — | — | — | — |
| | Phenoxyethanol | — | — | — | — | — | — | — | — | — | — |
| Others | Sodium hydroxide | — | q.s. | q.s. | q.s. | q.s. | q.s. | q.s. | — | q.s. | q.s. |
| | Hydrochloric acid | q.s. | — | — | — | — | — | — | q.s. | — | — |
| Content of active | Component (A) | 1 | 1 | 1 | 1 | 1 | 1 | 1 | 1 | 1 | 1 |
| | Component (C) | 0.1 | 0.2 | 1 | 5 | 10 | 1 | 1 | 1 | 1 | 1 |
| | (C)/(A) | 0.1 | 0.2 | 1 | 5 | 10 | 1 | 1 | 1 | 1 | 1 |
| | pH | 3 | 3 | 3 | 3 | 3 | 3 | 3 | 3 | 3 | 4 |
| Vividness of color of hair | Immediately after washing (Δc*1) | 0.6 | 0.5 | 1.2 | 1.3 | 1.5 | 11 | 1.5 | 1.0 | 1.5 | 1.0 |
| | After shampooing 14 times (Δc*2) | 0.3 | 0.4 | 1.0 | 0.9 | 0.9 | 0.8 | 1.2 | 0.9 | 1.3 | 0.6 |
| | Amount of change (\|Δc*2 − Δc*1\|) | 0.3 | 0.1 | 0.2 | 0.4 | 0.6 | 0.3 | 0.3 | 0.1 | 0.2 | 0.4 |

TABLE 1-continued

| | Component (mass %) | Example 11 | Example 12 | Comparative Example 1 | Comparative Example 2 | Comparative Example 3 | Comparative Example 4 | Comparative Example 5 | Comparative Example 6 |
|---|---|---|---|---|---|---|---|---|---|
| (A) | Epoxy-aminosilane copolymer mixture (*1) | 3.3 | 13.3 | Without post-treatment | Inverse procedure of Example 3 | 6.7 | 6.7 | 6.7 | — |
| (B) | Water | Balance | Balance | | | Balance | Balance | Balance | Balance |
| (C1) | Lactic acid | 4 | 1 | | | — | 1 | 1 | 1 |
| | Phosphoric acid | — | — | | | — | — | — | — |
| | Malic acid | — | — | | | — | — | — | — |
| | Succinic acid | — | — | | | — | — | — | — |
| | Citric acid | — | — | | | — | — | — | — |
| (D) | Ethanol | — | — | | | — | — | — | — |
| | Benzyl alcohol | — | — | | | — | — | — | — |
| | Phenoxyethanol | — | — | | | — | — | — | — |
| Others | Sodium hydroxide | q.s. | q.s. | | | — | — | q.s. | q.s. |
| | Hydrochloric acid | — | — | | | q.s | q.s. | — | — |
| Content of active | Component (A) | 0.5 | 2 | | | 1 | 1 | 1 | 0 |
| | Component (C) | 4 | 1 | | | 0 | 1 | 1 | 1 |
| | (C)/(A) | 8 | 0.5 | | | 0 | 0 | 1 | — |
| | pH | 3 | 3 | | | 3 | 5 | 7 | 3 |
| Vividness of color of hair | Immediately after washing (Δc*1) | 1.3 | 0.7 | Reference | −0.5 | 0.5 | 0.3 | −0.5 | 0 |
| | After shampooing 14 times (Δc*2) | 0.7 | 0.5 | Reference | 0.1 | −0.1 | 0.0 | −0.1 | −0.1 |
| | Amount of change (\|Δc*2 − Δc*1\|) | 0.6 | 0.2 | Reference | 0.6 | 0.6 | 0.3 | 0.4 | 0.1 |

*1Silsoft CLX-E (manufactured by Momentive Performance Materials Inc., polysilicone-29: 15 mass %)

TABLE 2

| | Component (mass %) | Example 13 | Example 14 | Example 15 | Example 16 | Example 17 | Example 18 |
|---|---|---|---|---|---|---|---|
| (A) | Epoxy-aminosilane copolymer mixture (*1) | 6.7 | 6.7 | 6.7 | 6.7 | 6.7 | 6.7 |
| (B) | Water | Balance | Balance | Balance | Balance | Balance | Balance |
| (C1) | Lactic acid | 1 | 1 | — | — | — | 1 |
| | Phosphoric acid | — | — | — | — | — | — |
| | Malic acid | — | — | 1 | — | — | — |
| | Succinic acid | — | — | — | 1 | — | — |
| | Citric acid | — | — | — | — | 1 | — |
| (D) | Ethanol | 20 | 20 | 20 | 20 | 20 | 5 |
| | Benzyl alcohol | — | — | — | — | — | 1 |
| | Phenoxyethanol | — | — | — | — | — | 1 |
| Others | Sodium hydroxide | q.s. | q.s. | q.s. | — | q.s. | q.s. |
| | Hydrochloric acid | — | — | — | q.s. | — | — |
| Content of active | Component (A) | 1 | 1 | 1 | 1 | 1 | 1 |
| | Component (B) | 1 | 1 | 1 | 1 | 1 | 1 |
| | (C)/(A) | 1 | 1 | 1 | 1 | 1 | 1 |
| | pH | 3 | 4 | 3 | 3 | 3 | 3 |
| Vividness of color of hair | Immediately after washing (Δc*1) | 1.9 | 1.2 | 1.8 | 1.2 | 1.9 | 1.2 |
| | After shampooing 14 times (Δc*2) | 1.3 | 1.1 | 1.6 | 1.1 | 1.7 | 0.7 |
| | Amount of change (\|Δc*2 − Δc*1\|) | 0.6 | 0.1 | 0.2 | 0.1 | 0.2 | 0.5 |

*1Silsoft CLX-E (manufactured by Momentive Performance Materials Inc., polysilicone-29: 15 mass %)

Examples 19 to 33 and Comparative Examples 7 to 12

The hair treatment agents shown in Tables 3 and 4 were prepared, and the vividness of the color of hair subjected to hair coloring treatment was evaluated in accordance with the following methods and criteria. Tables 3 and 4 also show the results.

[I: Hair Coloring Treatment]

A commercially available bleaching agent was applied to 1 g of Chinese black hair (manufactured by Beaulax Co., Ltd) at a bath ratio of 3.5:1 (bleaching agent: hair), and the hair was left standing at 40° C. for 40 minutes, then rinsed with water at about 40° C., washed with shampoo for evaluation, rinsed with water, and then dried with a dryer. Subsequently, measurement was performed on the CIE color coordinate system (L*, a*, b* and c*) with a D65 light source using a color-difference meter (Color-Difference Meter CR-400 manufactured by Konica Minolta Sensing, Ltd.), and only hair having a L* value of 22.5 to 25.1 (inclusive), a b* value of 10.0 to 13.3 (inclusive) and a c* value of 12.4 to 15.9 (inclusive) was selected, and used as bleached hair.

A commercially available hair color (a liquid obtained by mixing Topchic Color 5R and a Topchic Color Lotion 6% hydrogen peroxide product (each manufactured by Goldwell Company) at a mass ratio of 1:1 was used as a hair color) was applied to 1 g of the bleached hair at a bath ratio of 1:1 (hair color:hair), and the hair was left standing at 30° C. for 30 minutes, and then rinsed with water at about 40° C.

Thereafter, the hair was subjected to washing with shampoo for evaluation and rinsing with water two times. A conditioner for evaluation was then applied, and the hair was then rinsed with water at about 40° C., and wiped with a towel to remove excess water.

[II. Treatment with Hair Treatment Agent]

0.3 g of the hair treatment agent was applied to the wet hair after the hair dyeing (containing 0.4 g of water per g of dry hair), and uniformly spread throughout the hair, and the hair was dried with a dryer. Comparative Example 7 was a control without hair treatment after hair coloring treatment (control). In Comparative Example 8, II: treatment with the same hair treatment agent as in Example 21 was first performed and hair dyeing using the commercially available hair color described in [I: Hair coloring treatment] was then performed on the bleached hair described in [I: Hair coloring treatment]. Further, in Comparative Example 9, the bleached hair described in [I: Hair coloring treatment] was subjected to only hair dyeing with a hair color in which water at 7.7 mass % in the hair color was replaced by the component (A) and the component (C) in the same amounts as in Example 21 (Silsoft CLE-X at 6.7 mass % and monoethanolamine at 1 mass %).

[Evaluation on Vividness of Color of Hair (Measurement of Δc*1)]

The color of hair immediately after the hair treatment was measured on the CIE color coordinate system (L*, a*, b* and c*) with a D65 light source using a color-difference meter (Color-Difference Meter CR-400 manufactured by Konica Minolta Sensing, Ltd.). The color of hair of Comparative Example 7 without hair treatment after hair coloring treatment was similarly measured on the CIE color coordinate system (L*, a*, b* and c*). The value of Δc*1 was determined as an index of vividness of the color of hair by the following calculation.

$$\Delta c^{*}1 = (c^{*} \text{ value of hair immediately after hair treatment}) - (c^{*} \text{ value of hair of Comparative Example 7})$$

<Evaluation on Vividness of Color of Hair after Repeated Use of Shampoo (Measurement of Δc*2)>

The hair after the hair treatment was subjected to washing with shampoo for evaluation and rinsing with water 14 times. A conditioner for evaluation was then applied, and the hair was then rinsed with water at about 40° C., wiped with a towel to remove excess water, and dried with a dryer. The color of the obtained hair after repeated use of shampoo was measured on the CIE color coordinate system (L*, b* and c*) with a D65 light source using a color-difference meter (Color-Difference Meter CR-400 manufactured by Konica Minolta Sensing, Ltd.). The color of hair of Comparative Example 7 without hair treatment after hair coloring treatment was similarly measured on the CIE color coordinate system (L*, a*, b* and c*) after washing with shampoo was performed 14 times. The value of Δc*2 was determined as an index of vividness of the color of hair after repeated use of shampoo by the following calculation.

$$\Delta c^{*}2 = (c^{*} \text{ value of hair after washing with shampoo 14 times after hair treatment}) - (c^{*} \text{ value after washing of hair of Comparative Example 7 with shampoo 14 times})$$

TABLE 3

| Component | | Example | | | | | | | | |
|---|---|---|---|---|---|---|---|---|---|---|
| (mass %) | | 19 | 20 | 21 | 22 | 23 | 24 | 25 | 26 | 27 |
| (A) | Epoxy-aminosilane copolymer mixture (*1) | 6.7 | 6.7 | 6.7 | 6.7 | 6.7 | 6.7 | 6.7 | 3.3 | 13.3 |
| (B) | Water | Balance | Balance | Balance | Balance | Balance | Balance | Balance | Balance | Balance |
| (C2) | Monoethanolamine | 0.1 | 0.2 | 1 | 2 | 5 | — | — | 4 | 1 |
| | Aminomethyl propanol | — | — | — | — | — | 1 | — | — | — |
| | Tris(hydroxymethyl)aminomethane | — | — | — | — | — | — | 1 | — | — |
| (D) | Ethanol | — | — | — | — | — | — | — | — | — |
| | Dipropylene glycol | — | — | — | — | — | — | — | — | — |
| | Propylene glycol | — | — | — | — | — | — | — | — | — |
| Others | Carbomer (*2) | — | — | — | — | — | — | — | — | — |
| | Hydrochloric acid | q.s. | q.s. | q.s. | q.s. | q.s. | q.s. | q.s | q.s. | q.s. |
| Content | Component (A) | 1 | 1 | 1 | 1 | 1 | 1 | 1 | 0.5 | 2 |
| of active | Component (C) | 0.1 | 0.2 | 1 | 2 | 5 | 1 | 1 | 4 | 1 |
| | (C)/(A) | 0.1 | 0.2 | 1 | 2 | 5 | 1 | 1 | 8 | 0.5 |
| | pH | 9 | 9 | 9 | 9 | 9 | 9 | 9 | 9 | 9 |
| Vividness | Immediately after washing (Δc*1) | 1.4 | 0.7 | 0.6 | 0.7 | 0.5 | 0.6 | 05 | 0.4 | 0.7 |
| of color | After shampooing 14 times (Δc*2) | 0.8 | 0.8 | 0.4 | 0.3 | 0.2 | 0.4 | 03 | 0.2 | 0.7 |
| of hair | Amount of change (\|Δc*2 − Δc*1\|) | 0.6 | 0.1 | 0.2 | 0.4 | 0.3 | 0.2 | 02 | 0.2 | 0.0 |

| Component | | Example | Comparative Example | | | | | |
|---|---|---|---|---|---|---|---|---|
| (mass %) | | 28 | 7 | 8 | 9 | 10 | 11 | 12 |
| (A) | Epoxy-aminosilane copolymer mixture (*1) | 6.7 | Without post-treatment | Inverse procedure of Example 21 | Components (A) and (C) in the same amounts as in Example 21 are blended in hair dye | 6.7 | 6.7 | — |
| (B) | Water | Balance | | | | Balance | Balance | Balance |
| (C2) | Monoethanolamine | 1 | | | | — | 1 | 1 |
| | Aminomethyl propanol | — | | | | — | — | — |
| | Tris(hydroxymethyl)aminomethane | — | | | | — | — | — |
| (D) | Ethanol | — | | | | — | — | — |
| | Dipropylene glycol | — | | | | — | — | — |
| | Propylene glycol | — | | | | — | — | — |

TABLE 3-continued

| | | | | | | | | |
|---|---|---|---|---|---|---|---|---|
| Others | Carbomer (*2) | — | | | | — | — | — |
| | Hydrochloric acid | q.s. | | | | q.s. | q.s. | q.s. |
| Content of active | Component (A) | 1 | | | | 1 | 1 | 0 |
| | Component (C) | 1 | | | | 0 | 1 | 1 |
| | (C)/(A) | 1 | | | | 0 | 1 | — |
| | pH | 8 | | | | 9 | 7 | 9 |
| Vividness of color of hair | Immediately after washing (Δc*1) | 0.3 | Reference | 0 | 0 | 0.3 | 0.1 | 0 |
| | After shampooing 14 times (Δc*2) | 0.2 | Reference | −0.4 | −0.2 | 0 | 0 | −0.1 |
| | Amount of change (\|Δc*2 − Δc*1\|) | 0.1 | Reference | 0.4 | 0.2 | 0.3 | 0.1 | 0.1 |

*1Silsoft CLX-E (manufactured by Momentive Performance Materials Inc., polysilicone-29: 15 mass %)
*2CARBOPOL 981 (manufactured by Lubrizol Advanced Materials Inc.)

TABLE 4

| | Component | Example | | | | |
|---|---|---|---|---|---|---|
| | (mass %) | 29 | 30 | 31 | 32 | 33 |
| (A) | Epoxy-aminosilane copolymer mixture (*1) | 6.7 | 6.7 | 6.7 | 6.7 | 6.7 |
| (B) | Water | Balance | Balance | Balance | Balance | Balance |
| (C2) | Monoethanolamine | 1 | — | — | 1 | 1 |
| | Aminomethyl propanol | — | 1 | — | — | — |
| | Tris(hydroxymethyl)aminomethane | — | — | 1 | — | — |
| (D) | Ethanol | 20 | — | — | 20 | 20 |
| | Dipropylene glycol | — | 4 | — | — | — |
| | Propylene glycol | — | — | 4 | — | — |
| Others | Carbomer (*2) | — | — | — | 0.1 | 0.5 |
| | Hydrochloric acid | q.s. | q.s. | q.s. | q.s. | q.s. |
| Content of active | Component (A) | 1 | 1 | 1 | 1 | 1 |
| | Component (C) | 1 | 1 | 1 | 1 | 1 |
| | (C)/(A) | 1 | 1 | 1 | 1 | 1 |
| | pH | 9 | 9 | 9 | 9 | 9 |
| Vividness of color of hair | Immediately after washing (Δc*1) | 0.7 | 1.0 | 0.7 | 1.6 | 0.8 |
| | After shampooing 14 times (Δc*2) | 0.5 | 0.8 | 0.5 | 1.3 | 0.6 |
| | Amount of change (\|Δc*2 − Δc*1\|) | 0.2 | 0.2 | 0.2 | 0.3 | 0.2 |

*1Silsoft CLX-E (manufactured by Momentive Performance Materials Inc., polysilicone-29: 15 mass %)
*2CARBOPOL 981 (manufactured by Lubrizol Advanced Materials Inc.)

The invention claimed is:

1. A method for treating hair, the method comprising:

(1) applying a hair dye composition to hair to dye the hair; and (2) successively applying a hair treatment agent to the hair subjected to hair dyeing in the applying (1), wherein the hair treatment agent has a pH of 4 or less and comprises the following components:

(A) polysilicone-29 in an amount of 0.5% to 2% by weight;

(B) water;

(C) a pH adjuster which is one or more selected from the group consisting of phosphoric acid, succinic acid, lactic acid, malic acid and citric acid; and dipropylene glycol.

2. The method for treating hair according to claim 1, wherein the pH adjuster is one or more selected from the group consisting of lactic acid, malic acid and citric acid.

3. The method for treating hair according to claim 1, wherein a mass ratio of the component (C) to the component (A), (C)/(A), in the hair treatment agent is 0.05 or more and 15 or less.

4. The method for treating hair according to claim 1, wherein the hair treatment agent further comprises an organic solvent as component (D).

5. The method for treating hair according to claim 4, wherein the component (D) is one or more selected from the group consisting of linear alcohols having 1 to 4 carbon atoms and aromatic alcohols.

6. The method for treating hair according to claim 4, wherein a content of the component (D) in the hair treatment agent is 1 mass % or more and 40 mass % or less.

7. The method for treating hair according to claim 1, wherein the successively applying (2) does not include either a step of exposing the hair to an electromagnetic radiation using an apparatus for supplying an electromagnetic radiation or a step of mechanically reshaping the hair.

8. A method for improving chroma of a color of dyed hair, the method comprising carrying out (2) on hair after hair dyeing treatment:

(2) successively applying a hair treatment agent to hair after hair dyeing, wherein the hair treatment agent has a pH of 4 or less and comprises the following components:

(A) polysilicone-29 in an amount of 0.5% to 2% by weight;

(B) water;

(C) a pH adjuster which is one or more selected from the group consisting of phosphoric acid, succinic acid, lactic acid, malic acid and citric acid; and dipropylene glycol.

9. The method for treating hair according to claim 1, wherein the hair treatment agent comprises (C1) lactic acid.

10. The method for treating hair according to claim 8, wherein the hair treatment agent comprises (C1) lactic acid.

11. The method for treating hair according to claim 8, wherein a mass ratio of the component (C) to the component (A), (C)/(A), in the hair treatment agent is 0.05 or more and 15 or less.

* * * * *